(12) United States Patent
Paponneau

(10) Patent No.: US 6,808,538 B2
(45) Date of Patent: Oct. 26, 2004

(54) VERTEBRAL BODY SPACER HAVING VARIABLE WEDGED ENDPLATES

(75) Inventor: Francois Paponneau, Gradignan (FR)

(73) Assignee: Stryker Spine (FR)

( * ) Notice: Subject to any disclaimer, the term of this patent is extended or adjusted under 35 U.S.C. 154(b) by 246 days.

(21) Appl. No.: 10/099,693

(22) Filed: Mar. 15, 2002

(65) Prior Publication Data
US 2003/0176925 A1 Sep. 18, 2003

(51) Int. Cl.[7] .................................................. A61F 2/44
(52) U.S. Cl. .................................................. 623/17.16
(58) Field of Search ........................... 623/17.11, 17.14, 623/17.13, 17.15, 17.16

(56) References Cited

U.S. PATENT DOCUMENTS

| | | | |
|---|---|---|---|
| 4,309,777 A | | 1/1982 | Patil |
| 4,759,766 A | | 7/1988 | Buettner-Janz et al. |
| 4,863,477 A | | 9/1989 | Monson |
| 4,997,432 A | | 3/1991 | Keller |
| 5,401,269 A | * | 3/1995 | Buttner-Janz et al. ... 623/17.15 |
| 5,480,422 A | | 1/1996 | Bertagnoli |
| 5,534,029 A | | 7/1996 | Shima |
| 5,556,431 A | | 9/1996 | Buttner-Janz |
| 5,562,738 A | | 10/1996 | Boyd et al. |
| 5,895,428 A | * | 4/1999 | Berry ....................... 623/17.15 |
| 5,899,941 A | * | 5/1999 | Nishijima et al. ........ 623/17.15 |
| 5,989,291 A | | 11/1999 | Ralph et al. |
| 6,019,792 A | | 2/2000 | Cauthen |
| 6,086,613 A | * | 7/2000 | Camino et al. .......... 623/17.16 |
| 6,156,067 A | * | 12/2000 | Bryan et al. ............. 623/17.15 |
| 6,179,874 B1 | | 1/2001 | Cauthen |
| 6,368,350 B1 | | 4/2002 | Erickson et al. |
| 6,375,681 B1 | * | 4/2002 | Truscott .................. 623/17.11 |
| 6,682,562 B2 | * | 1/2004 | Viart et al. ............. 623/17.14 |
| 2001/0014826 A1 | * | 8/2001 | Biedermann et al. .... 623/17.11 |

FOREIGN PATENT DOCUMENTS

| | | |
|---|---|---|
| CH | 624573 | 8/1981 |
| DE | 2263842 | 12/1972 |
| DE | 3023353 A1 | 4/1981 |
| DE | 234609 A1 | 4/1986 |
| DE | 3529761 C2 | 7/1986 |
| DE | 239523 | 10/1986 |
| DE | 248018 A3 | 7/1987 |
| DE | 4417629 A1 | 1/1995 |
| EP | 0176728 B1 | 8/1985 |
| EP | 0630625 A2 | 5/1994 |
| WO | WO 93/10725 | 12/1992 |
| WO | WO 98/14142 | 12/1998 |
| WO | WO 99/53871 | 10/1999 |

* cited by examiner

*Primary Examiner*—Eduardo C. Robert
(74) *Attorney, Agent, or Firm*—Lerner, David, Littenberg, Krumholz & Mentlik, LLP

(57) ABSTRACT

A vertebral body spacer including a main body having an upper end including a first concave socket and a lower end including a second concave socket. The spacer includes a first endplate secured to the upper end of the main body, the first endplate having an underside with a convex projection adapted to form a ball and socket arrangement with the first concave socket. The spacer also includes, a second endplate secured to the lower end of the main body, the second endplate having an underside with a convex projection adapted to form a ball and socket arrangement with the second concave socket.

33 Claims, 9 Drawing Sheets

VERTEBRAL BODY SPACER HAVING VARIABLE WEDGED ENDPLATES

BACKGROUND OF THE INVENTION

The present invention is related to orthopedic implants and is more particularly related to spinal implants.

There have been many efforts directed to providing improved spinal implant devices. For example, U.S. Pat. No. 5,534,029 to Shima discloses an articulated vertebral body spacer including a pair of upper and lower joint pieces inserted between opposing vertebrae. The lower joint piece includes a convex portion formed on a central portion of its upper surface and having a convex sliding contact surface, and a stopper surface surrounding the convex portion. The upper joint piece includes a concave portion formed on a central portion of its lower surface and having a concave sliding contact surface which is in sliding contact with the convex sliding contact surface, and an abutment surface that surrounds the concave portion and abuts against the stopper surface. A cavity for allowing the upper joint piece to pivot in response to movement of the opposing vertebral bodies is formed between the abutment surface and the stopper surface.

DE 3529761 discloses a prosthesis for an intervertebral disc including two plates with a spacer disc therebetween. The two plates each have a concave center and a flat annular rim with spikes. The disc spacer has a convex center and a flat rim with an annular groove. The prosthesis is used for spanning the gap between opposing vertebral faces remaining firmly in place while permitting natural movement of the spine.

U.S. Pat. No. 4,997,432 to Keller discloses a prosthesis including two stop plates and a sliding body arranged therebetween. The outer surfaces of the stop plates have an essentially planar surface provided with tooth-like projection that penetrate into the vertebral bodies to fix the stop plates securely to the vertebral bodies. The opposite side surfaces of the stop plates include essentially spherical-shell-shaped recesses. The sliding core has a spherical-shell-shaped projections corresponding to the spherical-shell-shaped recesses. The stop plates are made of metal and the sliding body is made of a synthetic material.

U.S. Pat. No. 5,562,738 to Boyd et al. discloses an implant device having an ellipsoidally-shaped ball and socket oriented so that their greatest lengths are disposed along a first axis transverse to the anterior and posterior ends and respectively and their shortest lengths are disposed along a second axis which is perpendicular to the first axis along surface. A first joint surface is sloped away from socket while a second joint surface remains flat. The degree of slope determines the amount of relative rotation between joint surfaces and respectively, and the first joint surface is sloped to provide for up to 5° of lateral bending in either direction, up to 5° of extension and up to 5° of Flexion.

Finally, U.S. Pat. No. 5,556,431 to Buttner-Janz discloses an intervertebral disc endoprosthesis that is inserted between two vertebrae and has a bottom plate and a top plate that are connected to vertebral endplates. Referring to FIG. 1, the device includes prosthesis plates and prosthesis core cooperated via spherical surfaces. The core has an edge rim that limits its range of movement and insures, even under extreme conditions cohesion of the prosthesis. The endplate of the prosthesis plates, lie on the end surfaces of the vertebrae and are provided with teeth which, under load, penetrate into the vertebrae and thus secure the prosthesis in situ. Bore holes are arranged symmetrically on both side of the central plane, running from ventral to dorsal, of the vertebrae and in the area of the front edge of the prosthesis plates, to receive bone screws.

In spite of the above-noted advances in the art, there remains a need for an improved vertebral body spacer having enhanced stabilization and bone fusion characteristics. There is also a need for a vertebral body spacer that may be readily packed with bone growth material for facilitating fusion of the spacer with vertebral bodies. In addition, there is a need for a vertebral body spacer that is capable of obtaining a locking effect without the need for additional components such as locking screws.

SUMMARY OF THE INVENTION

In certain preferred embodiments of the present invention, a vertebral body spacer includes a main body having an upper end including a first concave socket and a lower end including a second concave socket. A first endplate is secured to the upper end of the main body and includes an underside having a convex projection adapted to form a ball and socket arrangement with the first concave socket. A second endplate is secured to the lower end of the main body and includes an underside having a convex projection adapted to form a ball and socket arrangement with the second concave socket.

In certain preferred embodiments, the upper end of the main body may include an upper edge defining first and second planes that are angled relative to one, and the lower end of the main body may include a lower edge defining first and second planes angled relative to one another. The first and second planes of the upper edge preferably intersect one another at an upper end apex and the first and second planes of the lower edge preferably intersect one another at a lower end apex. The upper apex desirably includes at least one retaining clip projecting therefrom for securing the first endplate to the upper end of the main body and the lower apex includes at least one retaining clip projecting therefrom for securing the second endplate to the lower end of the main body. In highly preferred embodiments, the upper apex includes a pair of retaining clips spaced from one another for pivotally securing the first endplate and the lower apex includes a pair of retaining clips spaced from one another for pivotally securing the second endplate. The first and second angled planes of the upper edge preferably limit pivotal movement of the first endplate and the first and second angled planes of the lower edge limit pivotal movement of the second endplate.

In certain preferred embodiments, the first endplate includes an upper side having teeth for engaging bone, such as the face of a vertebral body, and the second endplate includes an upper side having teeth for engaging bone. The first endplate also preferably has a central opening and a peripheral flange surrounding the central opening, the peripheral flange having at least one opening adapted to facilitate bone fusion. The second endplate, which may be substantially similar in size and shape as the first endplate, also preferably has a central opening and a peripheral flange surrounding the central opening, the peripheral flange having at least one opening adapted to facilitate bone fusion.

Each endplate preferably includes at least one retaining clip aperture adapted for receiving one of the retaining clips for securing the endplate with the main body.

In certain preferred embodiments, the main body is elongated and has an outer surface that is curved. In other preferred embodiments, the main body is substantially cylindrical in shape. The main body may also be elliptical, or have any other geometric shape. In one particular preferred embodiment, the main body has a longitudinal axis and the first and second concave sockets are coaxial about the longitudinal axis. The first and second angled planes at the upper end of the main body form an angle of approximately 5–25 degrees, and more preferably an angle of approximately 10–20 degrees. The main body desirably has a cross-sectional diameter of approximately 10–30 mm, and the endplates have a diameter of approximately 30–50 mm. In other preferred embodiments, the endplates have a diameter of approximately 35–40 mm.

The main body and the first and second endplates are desirably made of biocompatible materials, such as titanium, stainless steel, alloys and combinations thereof. The biocompatible material may also comprise polymeric materials.

The central opening of the first endplate desirably provides communication between the first socket and an exterior of the spacer. The central opening of the second endplate desirably provides communication between the second socket and an exterior of the spacer.

In operation, the spacer is positioned between the opposing faces of vertebrae. The endplates are pivotable when the spacer is in a first no-load state and are locked from pivotal movement when the spacer is in a second load state. Once pressure is applied to the endplates, the ball-and-socket joints are locked due to the blockage of the convex projections of the endplates in the concave sockets. After being positioned between two vertebrae, the endplates are desirably oriented for pivoting in a sagittal plane of a spine.

In other preferred embodiments of the present invention, a vertebral body spacer includes a main body having an upper end and a lower end, the upper end having a first concave socket and an upper edge surrounding the first concave socket defining first and second planes angled relative to one another, the lower end having a second concave socket and a lower edge surrounding the second concave socket defining first and second planes angled relative to one another. The spacer also preferably includes a first endplate pivotally secured to the upper end of the main body for pivoting between the first and second planes of the upper edge, the first endplate including an underside having a convex projection adapted to engage the first concave socket. The spacer also preferably includes a second endplate pivotally secured to the lower end of the main body for pivoting between the first and second planes of the lower edge, the second endplate including an underside having a convex projection adapted to engage the second concave socket. The convex projections preferably form ball and socket joints with the respective first and second concave sockets.

The upper edge desirably includes at least one retainer clip projecting therefrom for pivotally securing the first endplate to the main body, and the first endplate desirably includes at least one retainer clip aperture extending therethrough, the at least one retainer clip being passable therethrough for pivotally securing the first endplate to the main body. The first endplate preferably includes a series of apertures extending therethrough for receiving bone growth material and facilitating spinal fusion.

The lower edge desirably includes at least one retainer clip projecting therefrom for pivotally securing the second endplate to the main body, and the second endplate desirably includes at least one retainer clip aperture extending therethrough, the at least one retainer clip being passable therethrough for pivotally securing the second endplate to the main body. The second endplate preferably includes a series of apertures extending therethrough for receiving bone growth material and facilitating spinal fusion.

These and other preferred embodiments of the present invention will be described in more detail below.

DETAILED DESCRIPTION

Figure 1:
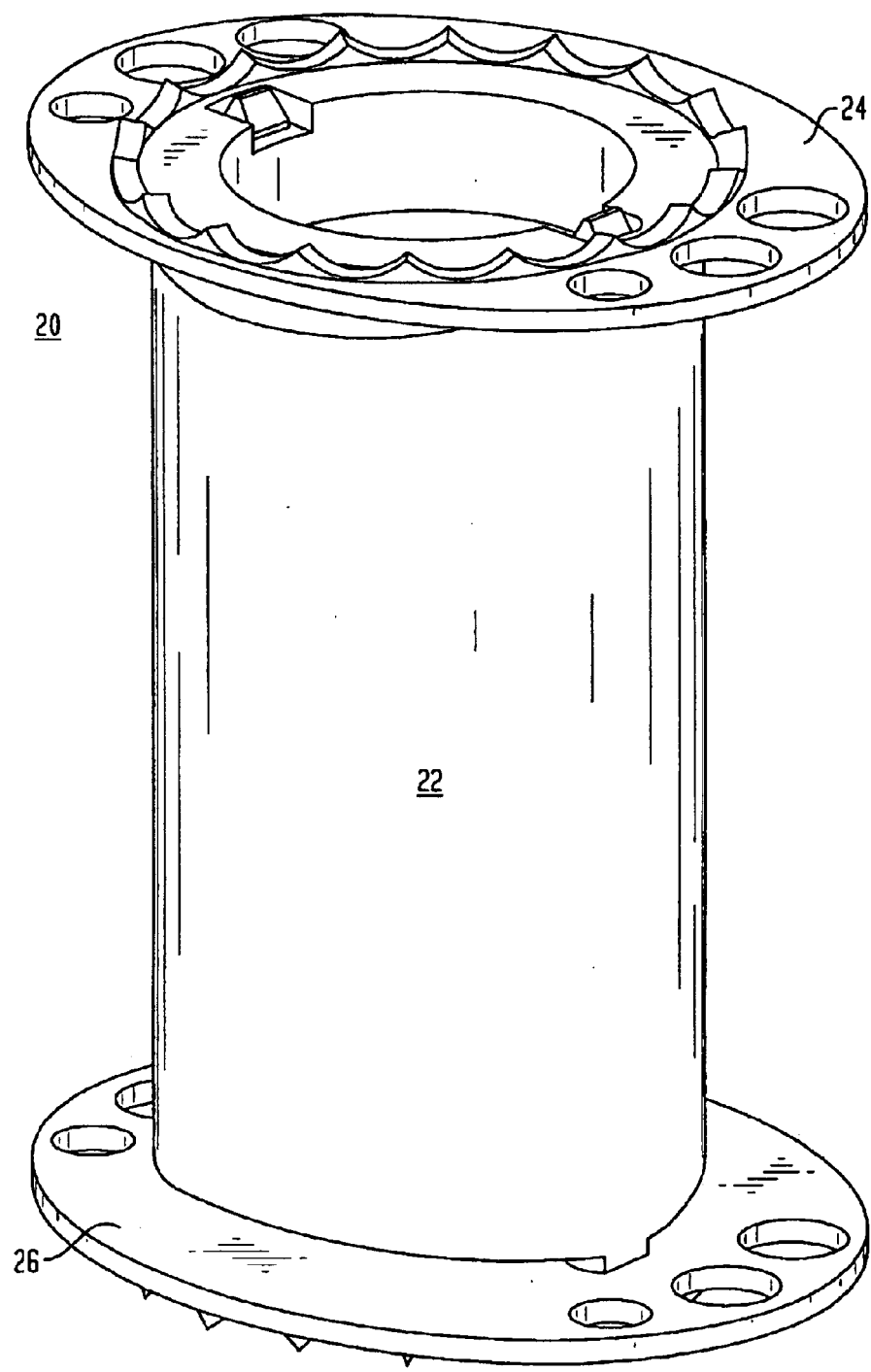
FIG. 1 shows a perspective view of a vertebral body spacer including a main body, a first endplate and a second endplate.

FIG. 1 shows a vertebral body spacer in accordance with certain preferred embodiments of the present invention. The spacer 20 includes a main body 22 having a first endplate 24 secured to an upper end of the main body and a second endplate 26 secured to a lower end of the main body. The spacer 20 is preferably made of a biocompatible material, such as a polymeric material, titanium, or stainless steel. Preferred materials may also include titanium alloys or stainless steel alloys.

Figure 2:
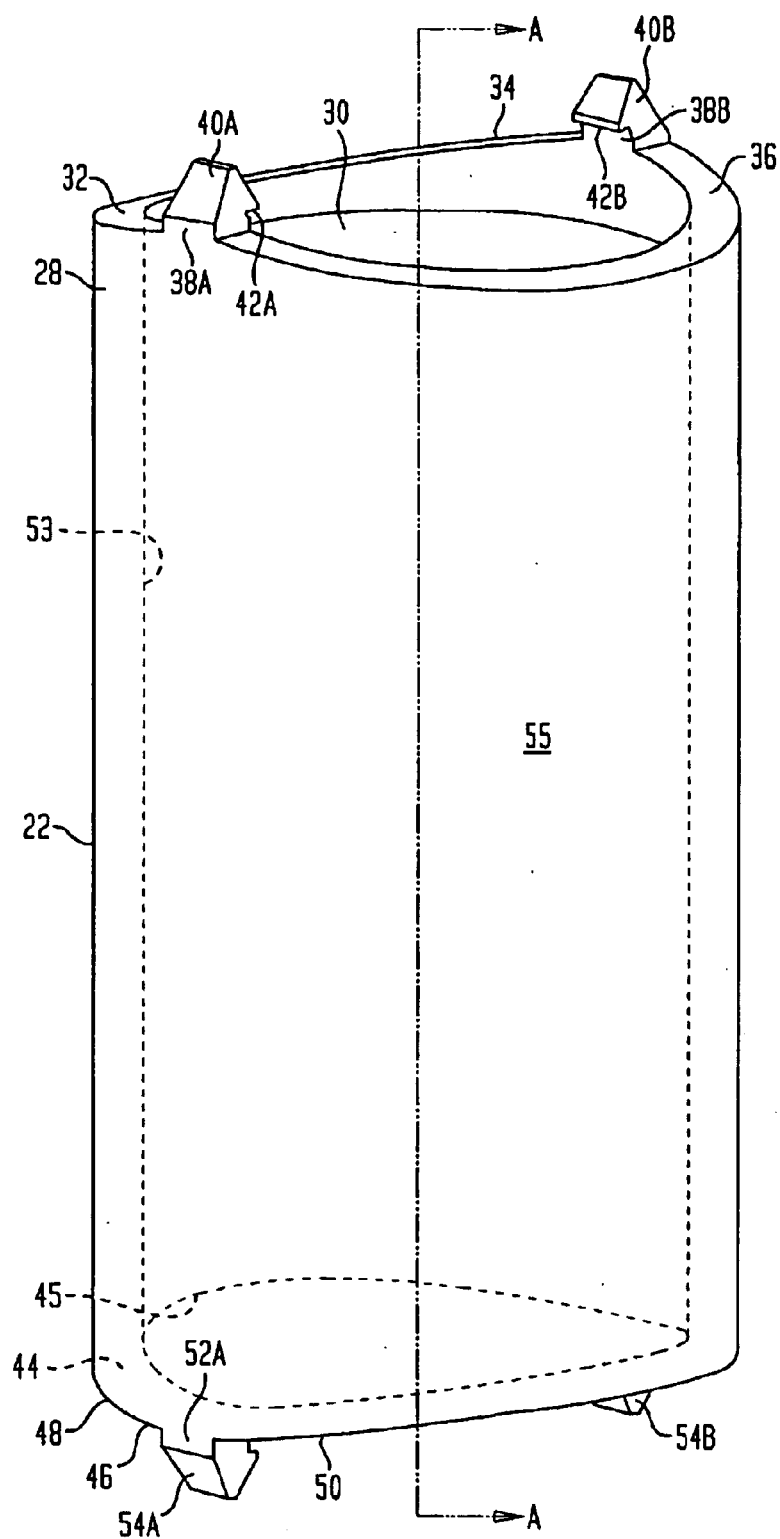
FIG. 2 shows a perspective view of the main body of FIG. 1 with the first and second endplates detached from the main body.

Referring to FIG. 2, in certain preferred embodiments, main body 22 has a longitudinal axis designated A—A. Main body 22 is preferably substantially cylindrical in shape and has an exterior surface that is coaxial with longitudinal axis A—A. In other preferred embodiments, main body 22 may be polygon-shaped in cross section. Main body 22 may have any geometric shape, such as the shape of an oval or ellipse. Main body 22 preferably has an upper end 28 with a first substantially concave-shaped socket 30 formed therein. The upper end 28 includes an upper edge 32 that surrounds the first concave socket 30. The upper edge 32 includes a first plane 34 and a second plane 36 that are angled relative to one another. The planes 34, 36 intersect at respective apexes 38A and 38B. Upper edge 32 also includes opposing first and second retaining clips 40A and 40B. First retaining clip 40A has an inwardly extending portion 42A and second retaining clip 40B has an inwardly extending projection 42B. As will be described in more detail below, the retaining clips 40A, 40B are designed to pass through retainer clip openings 28 that extend through the endplates shown in FIG. 1 for securing the endplates to the respective upper and lower ends of main body 22.

Referring to FIG. 2, main body 22 also has a lower end 44 including a substantially concave socket 45 and lower edge 46 that is substantially similar in design and shape to the first socket 30 at upper end 28. The lower edge 46 has a first inclined plane 48 and a second inclined plane 50 angled relative to one another, the inclined planes intersecting at opposing retaining clips 54A and 54B that are designed to pass through the retaining clip apertures of the second endplate. Main body 22 includes a substantially cylindrical interior wall 53 defining a hollow space 55 that extends between the upper end cavity 30 and the lower end cavity 45. In other embodiments, the interior wall 53 may be a flat surface or have any geometric shape defining a hollow space inside main body 22. As will be described in more detail below, the hollow space is adapted to receive bone growth material therein for facilitating fusion of the spacer 20 with vertebral bone.

Figure 3:
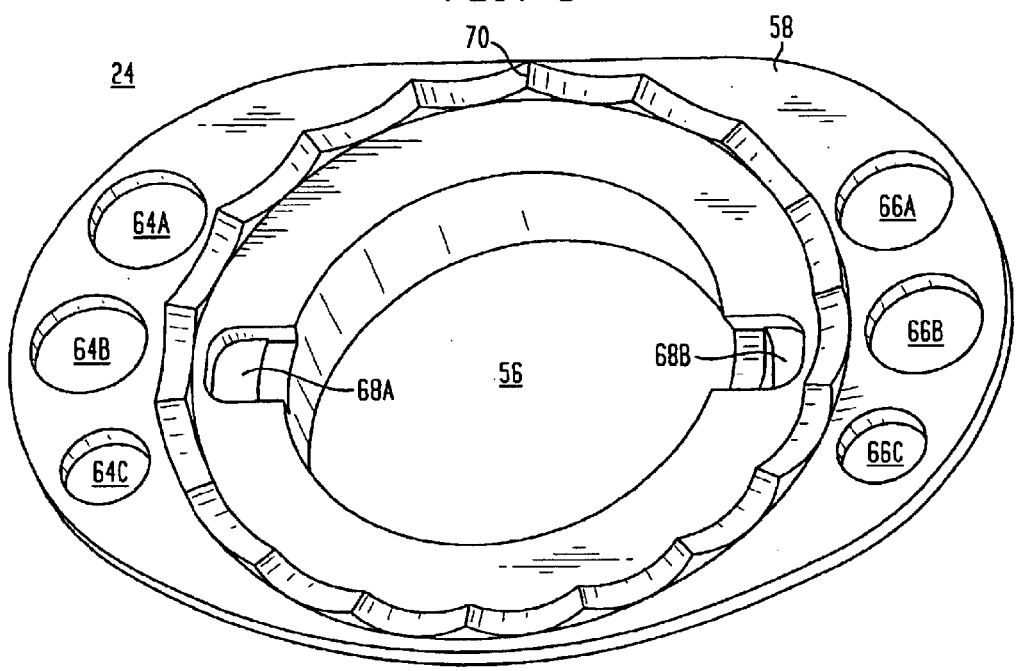
FIG. 3 shows a top view of the first endplate shown in FIG. 1.
Figure 4:
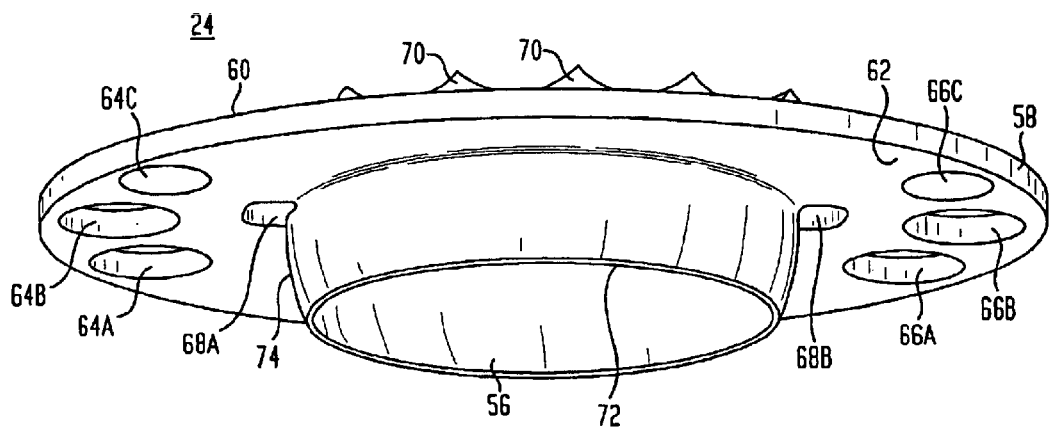
FIG. 4 shows an underside view of the endplate shown in FIG. 3.

FIG. 3 shows a top view of the first endplate 24. First endplate 24 includes a central opening 56 surrounded by a peripheral flange 58. Referring to FIGS. 3 and 4, the peripheral flange 58 has an upper surface 60 and a lower surface 62 opposite the upper surface 60. The peripheral flange also includes a series of apertures 64A–C and 66A–C. First endplate 24 also includes retainer clip apertures 68A and 68B that extend between upper and lower surfaces 60, 62 of flange 58. Upper surface 60 also includes a plurality of teeth 70 for anchoring or biting into bone such as the face of a vertebral body.

Referring to FIG. 4, first endplate 24 also includes a projection 72 extending from the lower surface 62 thereof. The projection 72 surrounds central opening 56 and has an exterior surface 74 that is substantially curved or convex. As will be described in more detail below, the substantially convex 74 projection facilitates pivotal movement of the first and second endplates 24, 26 relative to main body 22 (FIG. 1) when the endplates are not under load.

Figure 5:
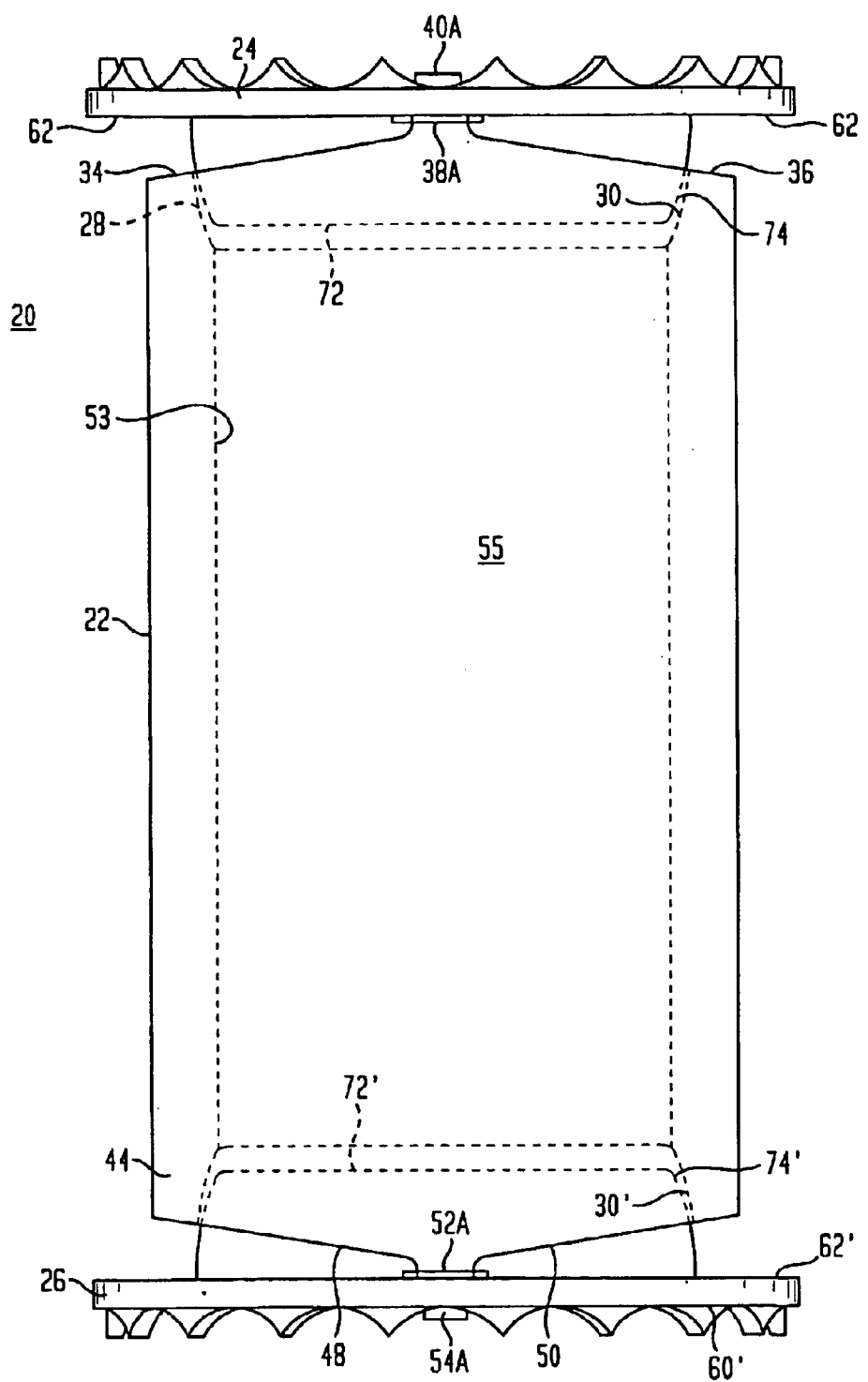
FIG. 5 shows a side elevation view of the vertebral body spacer of FIG. 1.

Referring to FIGS. 1 and 5, the vertebral body spacer 20 is assembled by juxtaposing the first endplate 24 with the upper end 28 of main body 22 and the second endplate 26 with the lower end 44 of main body 22. During assembly, the opposing retaining clips 40A, 40B are passed through the retaining clip apertures 68A, 68B (FIG. 3) of first endplate 24. In certain preferred embodiments, the retaining clips 40A, 40B are resilient so as to snap fit in place for pivotally connecting first endplate 24 with main upper end 28 of body 22. After the first endplate 24 has been snap fit in place, the convex exterior surface 74 of projection 72 is preferably in close engagement with first socket 30. As such, first endplate 24 is able to pivot about apex 38A, with the engagement of convex exterior surface 74 and first socket 30 guiding movement of first endplate 24. First endplate 24 is able to pivot in a counterclockwise direction approximately 10° until the lower surface 62 engages first plane upper edge 34 and in a clockwise direction approximately 10° until the lower surface 62 engages second plane edge 36. Thus, the range of pivotal movement of first endplate 24 relative to upper end 28 of main body 22 is between 15°–25°.

In a similar fashion, second endplate 26 is secured to retaining clips 54A, 54B at lower end 44 of main body 22. Second endplate 26 is assembled with main body 22 by passing retaining clips 54A, 54B through retaining clip apertures (not shown) extending between upper surface 60' and underside surface 62'. As second endplate 26 is assembled with lower end 44 of main body 22, convex exterior surface 74' of projection 72' closely engages second socket 30' for guiding pivotal movement of second endplate 26 about apex 52A.

Second endplate is pivotable approximately 10° in the counterclockwise direction until underside surface 62' engages second plane 50, and approximately 10° in the clockwise direction until underside surface 62' engages first plane 48.

Referring to FIG. 5, bone growth material (not shown) can be passed through the central openings of the first and second endplates 24, 26 for being disposed in hollow space 55. In certain preferred embodiments, the bone growth material completely fills the hollow space 55 and extends beyond the upper and lower ends 28, 44 of main body 22. In more preferred embodiments, the bone growth material is disposed in the central openings of the endplates 24, 26 for facilitating fusion with opposing vertebral bodies.

Figure 6:
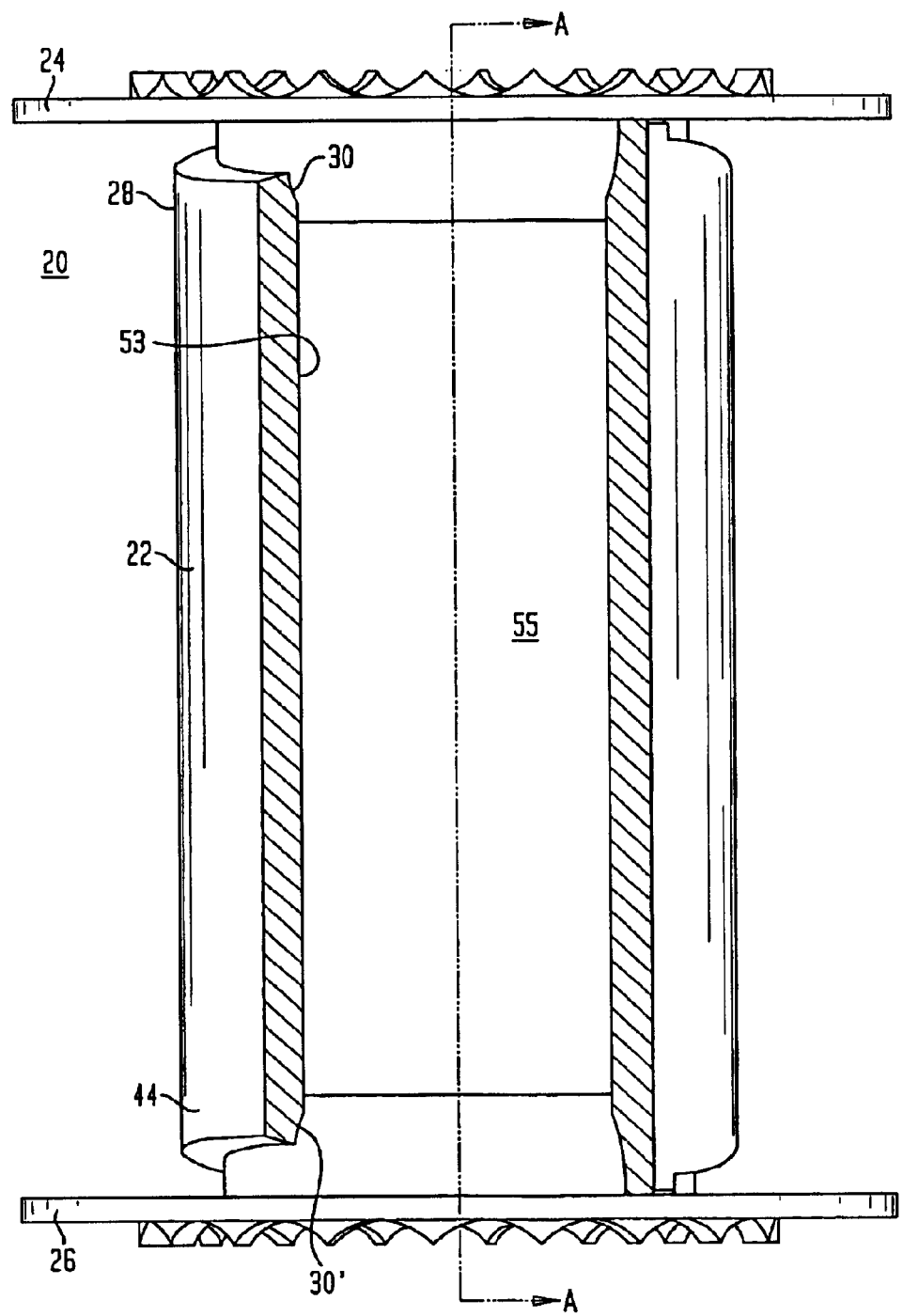
FIG. 6 shows a partial cut away view of the vertebral body spacer of FIG. 5.

FIG. 6 shows a partially cut-away view of the vertebral body spacer 20 of FIG. 1. As described above, main body 22 includes upper end 28 and lower end 44 remote therefrom. The upper end 28 of main body 22 has a first concave socket 30 formed therein and the lower end 44 has a second concave socket 30' formed therein. In preferred embodiments, the main body 22 is substantially hollow, with the hollow opening extending between first socket 30 and second socket 30'. After first and second endplates 24, 26 have been assembled with the respective upper and lower ends 28, 44 of main body 22, the endplates are free to pivot relative to main body so long as little or no load is placed upon the endplates. When the endplates are placed under load, however, the exterior surfaces 74, 74' of the projections are forced into close engagement with the sockets 30, 45 for locking the endplates in place from further movement.

Figure 7A:
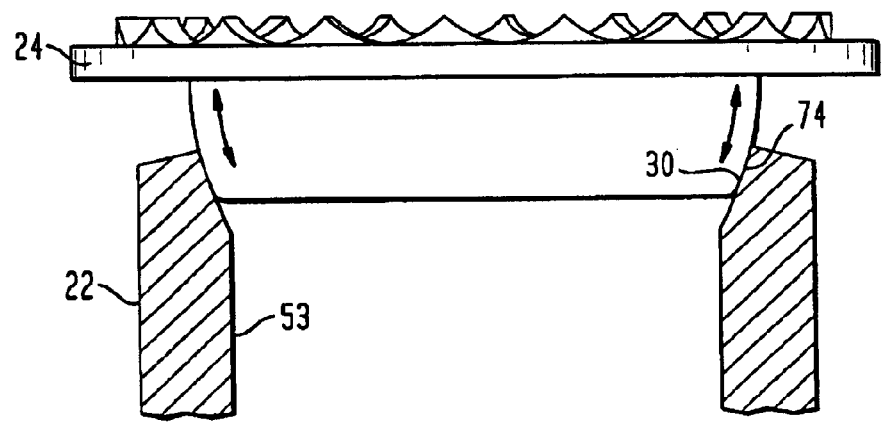
FIG. 7A shows the first endplate of FIG. 1 under a no-load condition.
Figure 7B:
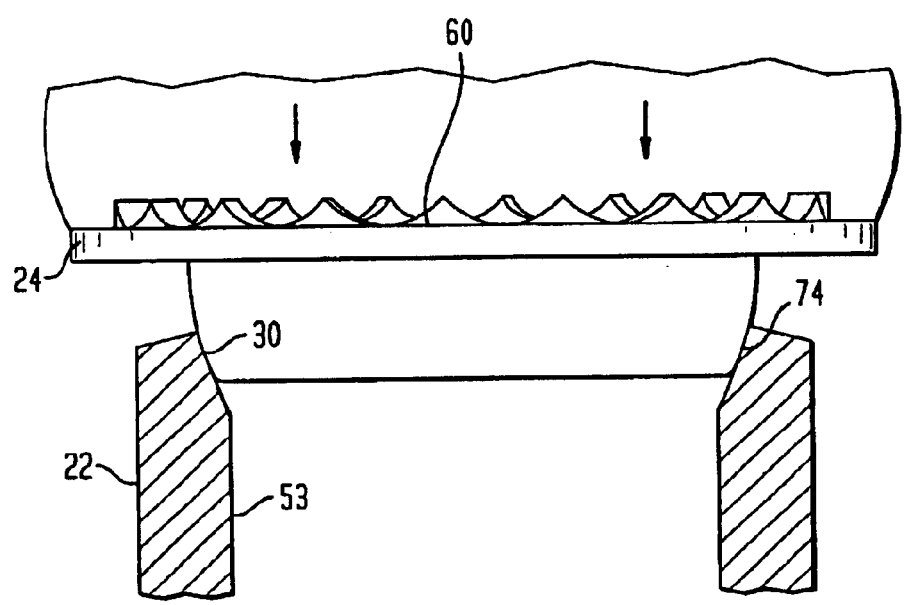
FIG. 7B shows the first endplate of FIG. 7A under a load condition.

FIG. 7A shows a fragmentary view of FIG. 6 before load is placed upon first endplate 24. Even though convex surface 74 of first endplate 24 is in direct contact with first socket 30, the first endplate remains free to pivot relative to first socket 30. Referring to FIG. 7B, after load has been placed upon upper surface 60 of first endplate 24, the convex surface 74 is urged into closer engagement with first socket 30, thereby locking first endplate 24 in place and preventing further pivotal movement of first endplate 24 relative to main body 22. Although not limited by any particular theory of operation, it is believed that once load is placed upon first endplate 24, friction forces lock first endplate from further pivotal movement relative to main body 22. First endplate 24 remains locked from further pivotal movement so long as first endplate remains under load. The second endplate 26 (FIG. 5) is also locked from further pivotal movement when under load in a manner similar to that described above for the first endplate 24. The above-described locking action can be attained without the need for additional parts such as locking screws that are typically required in prior art devices.

Once load has been removed from one of the endplates 24, 26, that particular endplate is once again free to pivot relative to main body 22 so long as it is not under load. Once load is reapplied, however, the endplate will once again be locked in place against further pivotal movement. Such locking and unlocking action will take place repeatedly during the life of the vertebral body spacer of the present invention.

Figure 8A:
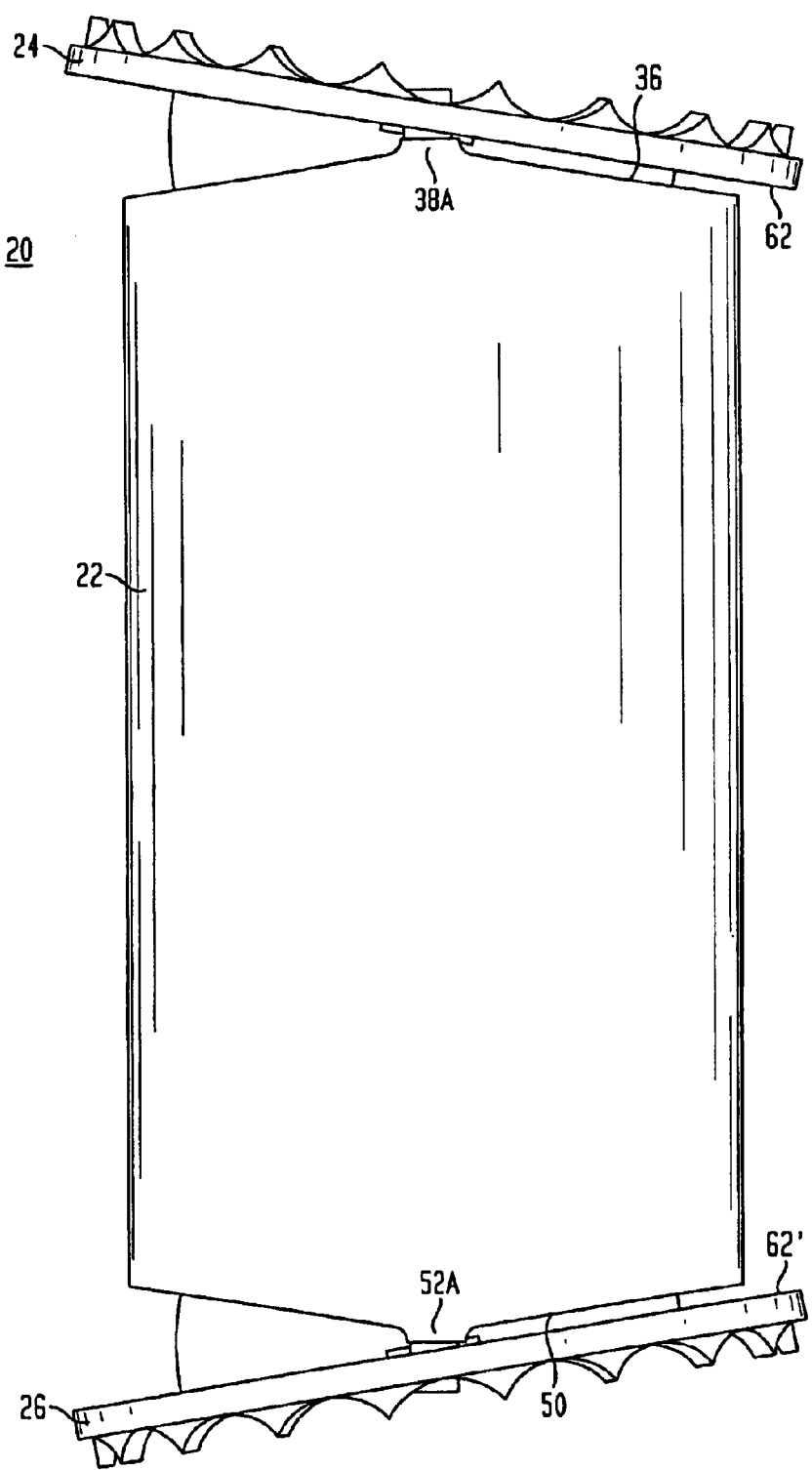
FIGS. 8A–8C show the vertebral body spacer of FIG. 5 with the first and second endplates pivoted to various angles relative to the main body.
Figure 8B:
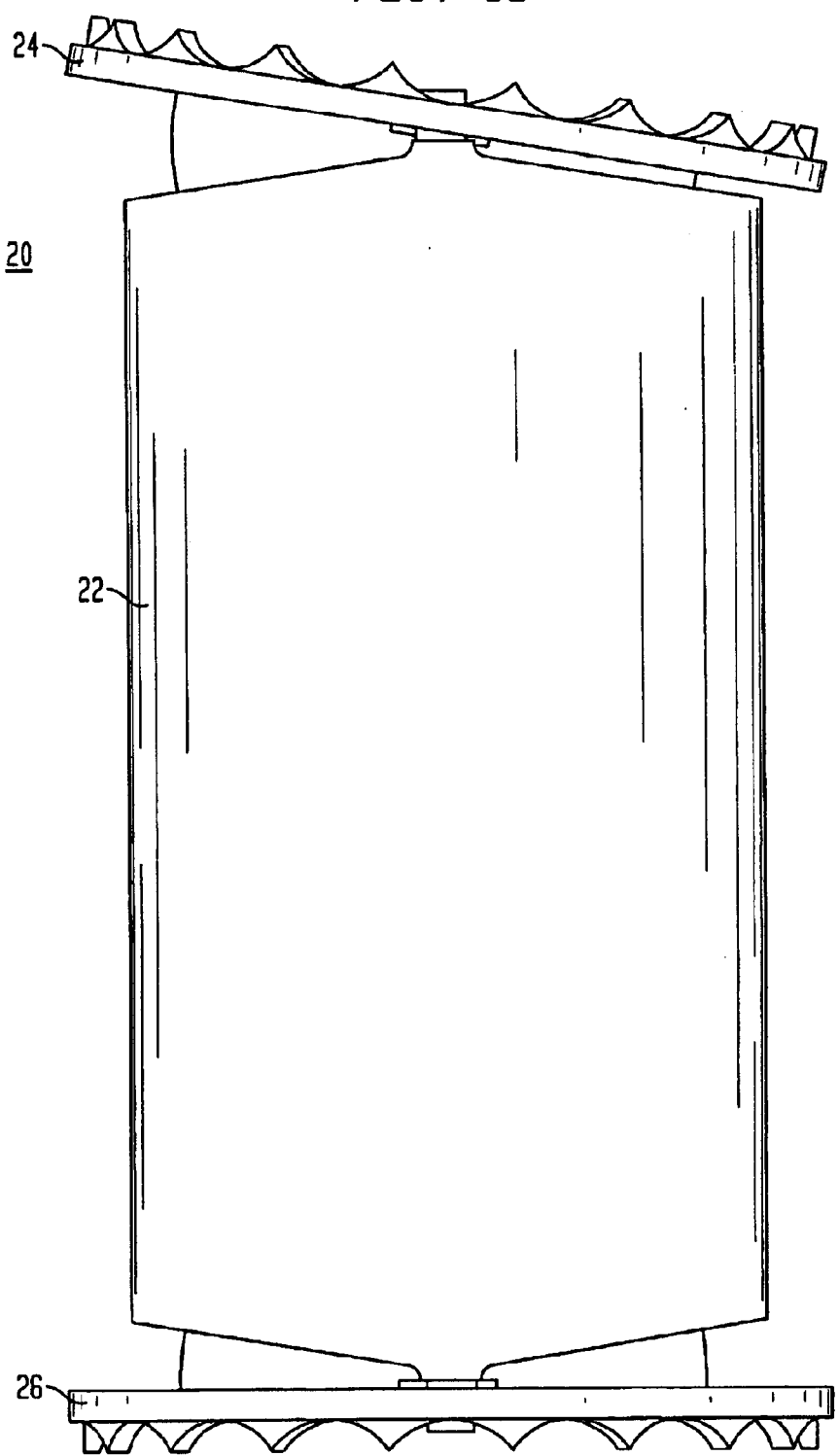
Figure 8C:
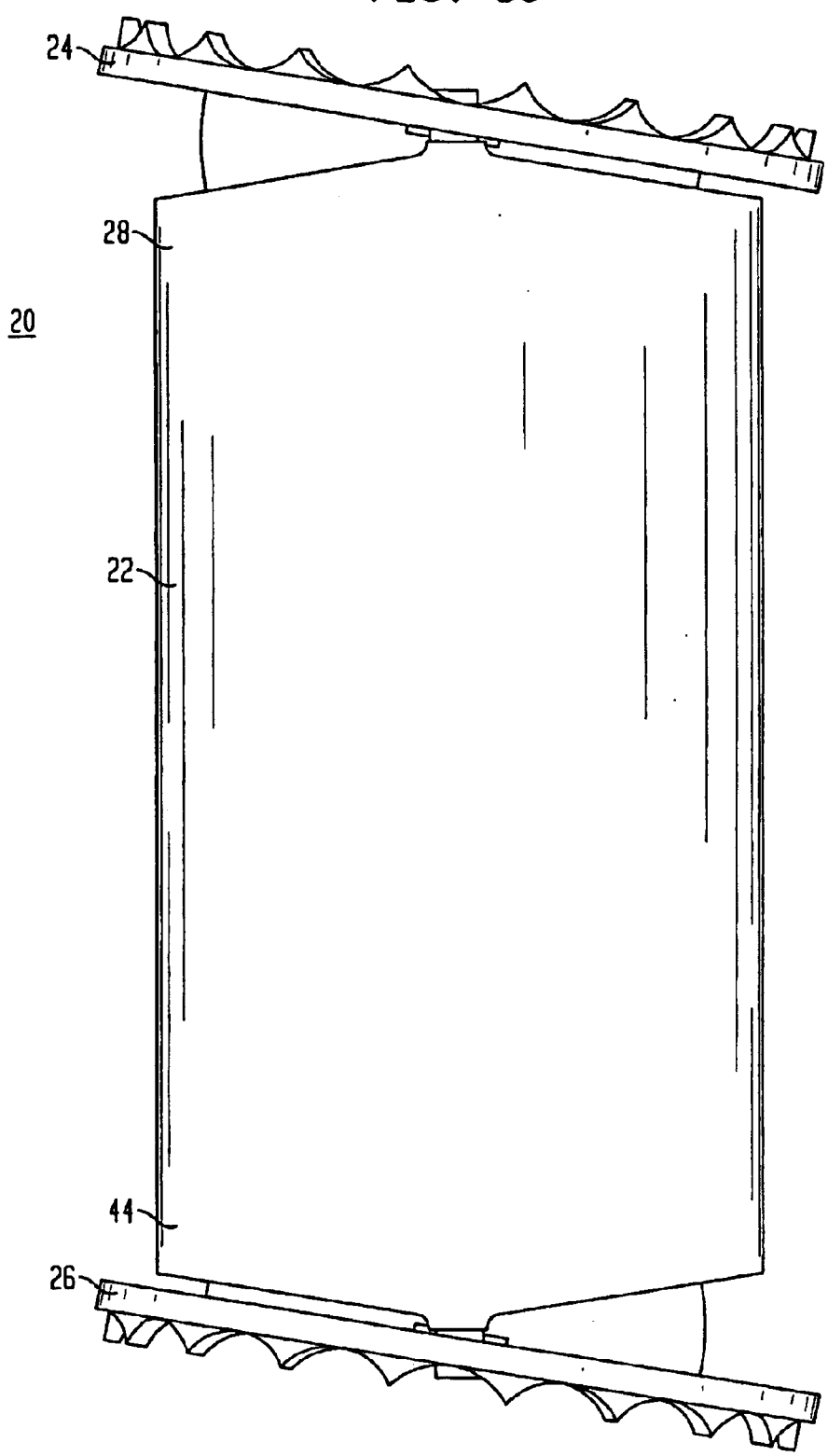

FIGS. 8A–8C show the range of pivotal movement of the first and second endplates 24, 26 relative to main body 22. In FIG. 8A first endplate 24 rotates in a clockwise direction around apex 38A until underside surface 62 engages second plane 36. Second endplate 26 is pivotable about apex 52A until underside surface 62' engages second plane 50.

FIG. 8B shows the vertebral body spacer 20 of FIG. 8A with first endplate 24A rotated in a fully clockwise orientation and second endplate 26 positioned equidistant between a fully clockwise rotation and a fully counterclockwise rotation. FIG. 8C shows the vertebral body spacer 20 of FIG. 8B with first endplate 24 fully rotated in a clockwise position and second endplate 26 fully rotated in a clockwise position.

Although not limited by any particular theory of operation, it is believed that the vertebral body spacer 20 of the present invention will provide an effective spacer between end faces of vertebral bodies. The spacer 20 of the present invention may span a gap present after one or more discs or vertebral bodies have been removed. The teeth 70 of the first and second endplates 24, 26 are designed to bite into the bony end faces of the vertebral bodies for holding the spacer 20 in place. In a first no-load state, when no load is applied to the end faces 24, 26, the end faces are free to pivot relative to the upper end 28 and lower end 44 of main body 22. Once a load is exerted upon either endplate 24, 26, however, the endplates are locked in place from further pivotal movement due to engagement of their convex exterior surfaces 74, 74' with the respective first and second sockets 30, 30'.

In other preferred embodiments, only one of the ends of the main body may have a pivotable endplate connected thereto, while the other end may be rigid or unmovable.

Although the invention herein has been described with reference to particular embodiments, it is to be understood that these embodiments are merely illustrative of the principles and applications of the present invention. It is therefore contemplated that numerous modifications may be made to the illustrated embodiments and that other arrangements may be made without departing from the spirit and scope of the present invention as defined by the appended claims.

What is claimed is:

1. A vertebral body spacer comprising:
   a main body having an upper end including a first concave socket and a lower end including a second concave socket, and a hollow space that extends between said first concave socket and said second concave socket;
   a first endplate secured to said upper end of said main body, wherein said first endplate includes an upper surface and an underside having a convex projection adapted to form a ball and socket arrangement with said first concave socket; wherein each of said endplates include an opening extending from the upper surface to the underside, said opening being in communication with said hollow space; and
   a second endplate secured to said lower end of said main body, wherein said second endplate includes an underside having a convex projection adapted to form a ball and socket arrangement with said second concave socket.

2. The spacer as claimed in claim 1, wherein said upper end includes an upper edge defining first and second planes angled relative to one another and said lower end includes a lower edge defining first and second planes angled relative to one another.

3. The spacer as claimed in claim 2, wherein said first and second planes of said upper edge intersect one another at an upper end apex and said first and second planes of said lower edge intersect one another an a lower end apex.

4. The spacer as claimed in claim 3, wherein said upper apex includes at least one retaining clip projecting therefrom for securing said first endplate to said upper end of said main body and said lower apex includes at least one retaining clip projecting therefrom for securing said second endplate to said lower end of said main body.

5. The spacer as claimed in claim 4, wherein said upper apex includes a pair of retaining clips spaced from one another for securing said first endplate and said lower apex includes a pair of retaining clips spaced from one another for securing said second endplate.

6. The spacer as claimed in claim 4, wherein said first and second angled planes of said upper edge limit pivotal movement of said first endplate and said first and second angled planes of said lower edge limit pivotal movement of said second endplate.

7. The spacer as claimed in claim 1, wherein said first endplate includes an upper side having teeth for engaging bone and said second endplate includes an upper side having teeth for engaging bone.

8. The spacer as claimed in claim 7, wherein said first endplate opening being a central opening and a peripheral flange surrounding said central opening, and wherein said peripheral flange has at least one opening adapted to receive bone growth material.

9. The spacer as claimed in claim 8, wherein said second endplate opening being a central opening and a peripheral flange surrounding said central opening, and wherein said peripheral flange has at least one opening adapted to receive bone growth material.

10. The spacer as claimed in claim 4, wherein each said endplate includes at least one retaining clip aperture adapted for receiving one of said retaining clips for securing said endplate with said main body.

11. The spacer as claimed in claim 1, wherein each said endplate has teeth adapted for anchoring said spacer into bone.

12. The spacer as claimed in claim 1, wherein said main body is elongated and has an at least partially curved outer surface.

13. The spacer as claimed in claim 1, wherein said main body has a longitudinal axis and said first and second concave sockets are coaxial about said longitudinal axis.

14. The spacer as claimed in claim 1, wherein said main body and said first and second endplates are made of biocompatible material.

15. The spacer as claimed in claim 14, wherein said biocompatible material is selected from the group consisting of titanium, stainless steel, alloys and combinations thereof.

16. The spacer as claimed in claim 14, wherein said biocompatible material comprises polymeric materials.

17. The spacer as claimed in claim 9, wherein said central opening of said first endplate provides communication between said first socket and an exterior of said spacer.

18. The spacer as claimed in claim 9, wherein said central opening of said second endplate provides communication between said second socket and an exterior of said spacer.

19. The spacer as claimed in claim 1, wherein said endplates are pivotable when said spacer is in a first no-load state and are locked from pivotal movement when said spacer is in a second load state.

20. The spacer as claimed in claim 2, wherein said first and second angled planes at said upper end of said main body form an angle of approximately 5–25 degrees.

21. The spacer as claimed in claim 20, wherein said first and second angled planes at said upper end of said main body form an angle of approximately 10–20 degrees.

22. The spacer as claimed in claim 1, wherein said endplates are oriented for pivoting in a sagittal plane of a spine.

23. The spacer as claimed in claim 1, wherein said main body has a cross-sectional diameter of approximately 10–30 mm.

24. The spacer as claimed in claim 1, wherein said endplates have a diameter of approximately 30–50 mm.

25. The spacer as claimed in claim 24, wherein said endplates have a diameter of approximately 35–40 mm.

26. A vertebral body spacer comprising:
- a main body including an upper end and a lower end, said upper end having a first concave socket and an upper edge surrounding said first concave socket defining first and second planes angled relative to one another, said lower end having a second concave socket and a lower edge surrounding said second concave socket defining first and second planes angled relative to one another;
- a first endplate pivotally secured to said upper end of said main body for pivoting between said first and second planes of said upper edge, said first endplate including an underside having a convex projection adapted to engage said first concave socket;
- a second endplate pivotally secured to said lower end of said main body for pivoting between said first and second planes of said lower edge, said second endplate including an underside having a convex projection adapted to engage said second concave socket.

27. The spacer as claimed in claim 26, wherein said convex projections form ball and socket joints with the respective said first and second concave sockets.

28. The spacer as claimed in claim 26, wherein said upper edge includes at least one retainer clip projecting therefrom for pivotally securing said first endplate to said main body.

29. The spacer as claimed in claim 28, wherein said first endplate includes at least one retainer clip aperture extending therethrough, and wherein said at least one retainer clip is passable therethrough.

30. The spacer as claimed in claim 28, wherein said first endplate includes a series of apertures extending therethrough for receiving bone growth material and facilitating spinal fusion.

31. The spacer as claimed in claim 26, wherein said lower edge includes at least one retainer clip projecting therefrom for pivotally securing said second endplate to said main body.

32. The spacer as claimed in claim 31, wherein said second endplate includes at least one retainer clip aperture extending therethrough, and wherein said at least one retainer clip is passable therethrough.

33. The spacer as claimed in claim 32, wherein said second endplate includes a series of apertures extending therethrough for receiving bone growth material and facilitating spinal fusion.

* * * * *

UNITED STATES PATENT AND TRADEMARK OFFICE
CERTIFICATE OF CORRECTION

PATENT NO. : 6,808,538 B2 Page 1 of 1
DATED : October 26, 2004
INVENTOR(S) : Francois Paponneau It is certified that error appears in the above-identified patent and that said Letters Patent is hereby corrected as shown below:

Column 1,
Line 49, delete "and" (first occurrence).

Signed and Sealed this

Twenty-first Day of June, 2005

JON W. DUDAS
*Director of the United States Patent and Trademark Office*